(12) United States Patent
Guckler et al.

(10) Patent No.: US 10,842,347 B2
(45) Date of Patent: Nov. 24, 2020

(54) MEDICAL APPARATUS HAVING IMPROVED ENERGY MANAGEMENT

(71) Applicant: Carl Zeiss Meditec AG, Jena (DE)

(72) Inventors: Roland Guckler, Ulm (DE); Martin Fanenbruck, Oberkochen (DE); Helge Jess, Oberkochen (DE); Peter Nakaji, Phoenix, AZ (US)

(73) Assignee: Carl Zeiss Meditec AG, Jena (DE)

( * ) Notice: Subject to any disclaimer, the term of this patent is extended or adjusted under 35 U.S.C. 154(b) by 401 days.

(21) Appl. No.: 15/721,000

(22) Filed: Sep. 29, 2017

(65) Prior Publication Data

US 2018/0092511 A1 Apr. 5, 2018

Related U.S. Application Data

(60) Provisional application No. 62/402,035, filed on Sep. 30, 2016.

(30) Foreign Application Priority Data

Oct. 21, 2016 (DE) .................. 10 2016 220 698

(51) Int. Cl.
*A61B 1/00* (2006.01)
*A61B 90/00* (2016.01)
*A61B 5/06* (2006.01)

(52) U.S. Cl.
CPC ...... *A61B 1/00025* (2013.01); *A61B 1/00062* (2013.01); *A61B 90/08* (2016.02);
(Continued)

(58) Field of Classification Search
CPC combination set(s) only.
See application file for complete search history.

(56) References Cited

U.S. PATENT DOCUMENTS

| 9,037,199 | B1* | 5/2015 | Stogaitis | H04W 52/0254 |
| | | | | 455/574 |
| 2001/0032059 | A1* | 10/2001 | Kelly, Jr. | A61B 5/0002 |
| | | | | 702/150 |
| 2006/0155174 | A1* | 7/2006 | Glukhovsky | A61B 1/00036 |
| | | | | 600/301 |

(Continued)

FOREIGN PATENT DOCUMENTS

| DE | 102009017811 A1 * | 10/2010 | ......... A61B 1/00036 |
| DE | 102009017811 A1 | 10/2010 | |

(Continued)

OTHER PUBLICATIONS

English translation and First Office Action of the German Patent and Trademark Office dated Jul. 6, 2017 of German application 102016220698.2 on which a claim of priority is based.

*Primary Examiner* — John P Leubecker
*Assistant Examiner* — Shankar Raj Ghimire
(74) *Attorney, Agent, or Firm* — Walter Ottesen, P.A.

(57) ABSTRACT

A medical apparatus includes a control device, a motion sensor, via which a motion value is determinable, a position sensor, via which an angular position in space is detectable, and a time measuring device, via which a time interval is determinable. The control device is embodied in such a way that a switch-off signal is producible if, during the entire time interval, the motion value remains below a threshold and, at the same time, the position sensor detects an inclination angle relative to a repository plane that lies in a defined repository angle range.

11 Claims, 4 Drawing Sheets

(52) U.S. Cl.
CPC ......... *A61B 5/067* (2013.01); *A61B 2090/067* (2016.02); *A61B 2560/0209* (2013.01); *A61M 2205/3561* (2013.01); *A61M 2205/36* (2013.01)

(56) References Cited

U.S. PATENT DOCUMENTS

| | | | | |
|---|---|---|---|---|
| 2010/0130818 | A1* | 5/2010 | Jung | A61B 1/00006 600/109 |
| 2010/0308994 | A1* | 12/2010 | Luemkemann | A61F 9/008 340/540 |
| 2011/0082334 | A1* | 4/2011 | Dolt | A61B 1/045 600/104 |
| 2011/0184239 | A1* | 7/2011 | Wright | A61B 1/00016 600/118 |
| 2012/0112726 | A1* | 5/2012 | Kaihori | A61B 1/041 323/299 |
| 2012/0178991 | A1* | 7/2012 | Clark | A61B 1/00036 600/109 |
| 2014/0012078 | A1* | 1/2014 | Coussa | A61B 1/00036 600/109 |
| 2015/0094544 | A1* | 4/2015 | Spolin | A61B 5/7275 600/301 |
| 2017/0202591 | A1* | 7/2017 | Shelton, IV | A61B 18/1445 |
| 2017/0252091 | A1* | 9/2017 | Honda | A61B 18/1445 |
| 2017/0296043 | A1* | 10/2017 | On | A61B 1/00013 |

FOREIGN PATENT DOCUMENTS

| | | |
|---|---|---|
| DE | 102012009749 A1 | 11/2013 |
| EP | 2664271 A1 | 11/2013 |
| WO | 2009130666 A1 | 10/2009 |

* cited by examiner

MEDICAL APPARATUS HAVING IMPROVED ENERGY MANAGEMENT

CROSS REFERENCE TO RELATED APPLICATIONS

This application claims priority of U.S. provisional patent application No. 62/402,035, filed Sep. 30, 2016 and German patent application 10 2016 220 698.2, filed Oct. 21, 2016, and the entire content of both applications is incorporated herein by reference.

FIELD OF THE INVENTION

The invention relates to a medical apparatus. A medical apparatus is an electronic apparatus that is used in an examination of, or an operation on, a patient.

BACKGROUND OF THE INVENTION

In an operation situation, it may be the case that medical apparatuses are used multiple times for a temporally restricted period of time and not required between these periods of time. While the user, for example a surgeon, naturally activates a medical apparatus or a function on this medical apparatus before use in an operation situation, switching the apparatus off after use is sometimes forgotten about. It may be the case that the apparatus remains switched on when the apparatus is deposited again.

This leads to the medical apparatus heating up and a high energy consumption. It may be necessary to provide measures for cooling the apparatus. If the medical apparatus includes a light source, the light energy of the illumination, should the latter be directed at a location for a relatively long period of time, may effect a thermal load or damage of the illuminated location. By way of example, a high light power can burn holes into sterile drapes and, as a consequence, endanger the sterility of the apparatus or, in a worst-case scenario, lead to the development of a fire. If the apparatus includes a power supply by way of a battery or an accumulator, the possible period of use is moreover disadvantageously shortened.

SUMMARY OF THE INVENTION

It is an object of the invention to provide a medical apparatus which has an improved energy management and which overcomes aforementioned disadvantages.

The object can, for example, be achieved by a medical apparatus having: a control device; a motion sensor configured to determine a motion value; a position sensor configured to detect an angular position in space; a time measuring device configured to determine a time interval; and, the control device being configured to generate a switch-off signal if, during the entirety of the time interval, the motion value remains below a threshold and, at the same time, the position sensor detects an inclination angle relative to a repository plane that lies in a defined repository angle range.

The object can, for example, also be achieved by a method for triggering a switch-off signal for a medical apparatus. The medical device includes a control device, a motion sensor, a position sensor and a time measuring device. The method includes the steps: a. determining a motion value via the motion sensor; b. comparing the motion value to a threshold; c. determining an inclination angle relative to a repository plane via the position sensor; d. comparing the inclination angle to a defined repository angle range; e. determining a time interval; and, f. triggering the switch-off signal if, during the entire time interval, the motion value remains below the threshold and, at the same time, the inclination angle lies in the repository angle range.

According to an embodiment of the invention, a medical apparatus includes a control device, a motion sensor, via which a motion value is determinable, a position sensor, via which an angular position in space is detectable, and a time measuring device, via which a time interval is determinable. The control device is embodied in such a way that a switch-off signal is producible if, during the entire time interval, the motion value remains below a threshold and, at the same time, the position sensor detects an inclination angle relative to a repository plane that lies in a defined repository angle range.

The medical apparatus includes a control device, a motion sensor, a position sensor and a time measuring device. The movement or motion sensor is configured to identify a movement of the apparatus and generate a motion value that is electronically evaluable, the motion value being able to be evaluated by the control device. By way of example, a movement is characterized by a change in location and/or a change in angle of the apparatus in space. A movement can be uniform or include an acceleration. A movement can also be detected if it is very small.

The position sensor can determine an angular position in space. The position sensor does not determine an absolute position in space; instead, the position sensor is embodied to determine a relative inclination angle in relation to a reference plane. If the position sensor determines an angular position parallel to, or in, this reference plane, the angle deviation relative to the reference plane is zero. An angle relative to this reference plane is referred to as an inclination angle. The inclination angle spans a second plane that is arranged perpendicular to the reference plane. The inclination angle relative to the reference plane is transmitted to the control device. A plane in which the medical apparatus can be deposited is defined as a reference plane. This reference plane is therefore referred to as repository plane in this application. Here, the inclination angle that is determined by the position sensor is independent of the position in space at which the repository plane is defined since the inclination angle is identical for all planes that are parallel to this repository plane.

The medical apparatus further includes a timer or time measuring device, via which a time interval can be measured. A time interval is a time duration or a period of time with a start time and an end time.

For the control device to produce a switch-off signal, the following two conditions must be satisfied continuously during the entire time interval: the motion value remains below a threshold and, at the same time, the position sensor detects an inclination angle relative to a repository plane that lies in a defined repository angle range.

Thus, a switch-off signal is only activated automatically if a combination of motion detection and inclination angle detection, for example as a repository position in a repository, is identified without interruption over a certain time interval by the motion sensor and the position sensor. Consequently, a switch-off signal is only activated once the apparatus has been deposited in a defined repository position over the time interval and is not moved at the same time.

It is necessary to ensure that the medical apparatus remains switched on while in use. The medical apparatus is in use when it is moved, in particular when it is guided by hand. As a result, the motion sensor detects a motion value that lies above a threshold. The medical apparatus remains switched on.

If the medical apparatus is not moved, or only moved slightly, over a relatively long period of time, for example when it is fastened in a holder or held, for a long time, at a specific position by a user during an operation, it may be the case that no movement is detected and the determined motion value remains below the threshold for a predetermined minimum period of time.

However, since the medical apparatus is not in a repository position, the apparatus is consequently oriented in an angle range that lies outside of the defined repository angle range. Since it is arranged at an inclination angle that deviates from a repository position, the position sensor consequently detects an inclination angle relative to the repository plane that lies outside of a defined repository angle range. As a result, the aforementioned second condition has not been satisfied and the medical apparatus remains switched on.

Consequently, the detection of the inclination angle ensures that there cannot be an inadvertent deactivation of the medical apparatus. The apparatus also remains switched on if the medical apparatus is deposited for a short period of time that is shorter than the predetermined interval, for example if it is deposited and picked up again shortly thereafter.

The definition of a repository angle range facilitates a reliable production of the switch-off signal, even if the medical apparatus is positioned on the repository plane in a manner that is tilted by an angle, for example if, with a corner or an edge, it is placed on a different article. Likewise, the repository plane can be arranged at a specific angle relative to a horizontal plane. The repository plane can be any plane in space. The repository plane and the repository angle range are definable by the producer of the medical apparatus and/or by the user.

As a result of the threshold, very small movements, for example vibrations on a repository surface, are not detected as movements and prevent the activation of a switch-off signal.

In this way, a switch-off signal is reliably produced if the medical apparatus should be deposited for a period of time that is greater than the defined time interval. The switch-off signal brings about a shutdown of the medical apparatus. Advantageously, this shutdown reduces the energy consumption. The apparatus does not produce any heat and a possibly present light source is switched off. The period of application and service life of the medical apparatus are increased.

In an embodiment of the invention, the repository plane is a plane perpendicular to a vertical direction.

A vertical direction is a vector in the direction of the gravity acceleration and points into the direction of the center of the Earth. As a consequence, a vertical direction can be determined very easily by a position sensor. Consequently, a repository plane that is arranged perpendicular to this vertical direction forms a horizontal plane that is parallel to the Earth's surface. A medical apparatus can be deposited safely if the repository plane has a horizontal alignment.

In an embodiment of the invention, the absolute value of the defined repository angle range has a value of between 0° and 10°.

When the medical apparatus is deposited on a repository plane, the apparatus may tilt and assume various angular positions which, nevertheless, form a repository position. The repository plane may likewise have a slight angle. As a result of a repository angle range between 0° and 10°, it is possible to reliably identify a repository position and produce a switch-off signal.

In an embodiment of the invention, the absolute value of the defined repository angle range has a value of between 0° and 5°.

A very narrow tolerance for the defined repository angle range is advantageous if the medical apparatus is placed in an arrangement provided therefor.

In an embodiment, the medical apparatus is an endoscope.

An endoscope is a handheld medical apparatus which can be used in various positions. It is advantageously possible to integrate a motion sensor and/or a position sensor into an endoscope. An endoscope may have an illumination unit with a light source. Advantageously, the light source can be switched off by the switch-off signal in order to reduce a light exposure. A shutdown reduces the energy consumption and a possible production of heat. The period of application and service life of the medical apparatus are increased.

In an embodiment of the invention, the time interval is between 30 seconds and 60 seconds.

Advantageously, this prevents an early shutdown in the case of a short duration of less than 30 seconds of being deposited, for example if the medical apparatus is picked up again after this short duration of being deposited. If the switch-off signal is triggered after a time interval that lies between 30 and 60 seconds, an unnecessary energy consumption is significantly reduced. This time interval is ideal for surgical use.

In an embodiment of the invention, the time interval is between 30 seconds and 40 seconds.

Advantageously, the energy management can be optimized even further by a time interval of between 30 seconds and 40 seconds. The availability of the medical apparatus increases.

In an embodiment of the invention, the motion sensor and the position sensor are formed by a single three-axis gyro sensor.

Advantageously, the three-axis gyro sensor can simultaneously detect the motion value and the inclination angle. As a result, a single sensor can form the motion sensor and the position sensor. Gyro sensors can have a very small configuration and are cost effective.

In an embodiment, the medical apparatus includes an image capturing system and the motion value is determinable by analyzing the images provided by the image capturing system.

An image capturing system can record images in a temporal sequence. From this, a motion value can be derived in the control device, for example by way of image processing software. Advantageously, a motion value which is independent of a vertical direction can be produced in this way. In this way, the image capturing system forms a motion sensor. The position sensor need not be used for determining a motion value.

In an embodiment of the invention, the medical apparatus includes a metal sensor or a Hall sensor.

A metal sensor can advantageously detect a metallic repository surface. A Hall sensor can advantageously detect a repository position that has magnetic properties or includes a magnet. As a result, it is possible to specify the identification of a repository position.

In an embodiment of the invention, the power supply is wireless and includes a battery or an accumulator.

In the case of medical apparatuses that are operated by batteries or accumulators, the use duration can be significantly increased if the apparatuses are deactivated by a switch-off signal when not in use. It is possible to avoid a change of the power source, which may unnecessarily increase the operation duration. Advantageously, a longer battery or accumulator service life reduces the environmental pollution and the operating costs.

In an embodiment, a standby mode is activatable after triggering the switch-off signal.

Reactivation of the medical apparatus can be carried out very quickly in a standby mode. Advantageously, the position sensor can be used for identifying the apparatus being picked up again, for example if the inclination angle has a value that lies outside of the repository angle range.

In an embodiment, a complete shutdown of the medical apparatus is effectable after triggering the switch-off signal.

A complete shutdown brings about the largest possible energy saving since no standby current is present. An accidental restart, for example by way of a hit on the apparatus that is detectable by the motion sensor, is avoided. Likewise, there is no unwanted activation if the apparatus is displaced on the repository arrangement and deposited again at a different position.

In an embodiment, a reactivation of the medical apparatus is only possible by way of a reactivation operating element.

Advantageously, this renders an unwanted reactivation avoidable. Only once a user picks the medical apparatus up again and actuates the reactivation operating element, for example a switch-on button, is the apparatus switched on again.

According to an embodiment of the invention, a method for triggering a switch-off signal for a medical apparatus having a control device, a motion sensor, a position sensor and a time measuring device includes the following steps:

a. determining a motion value by the motion sensor,
b. comparing the motion value to a threshold,
c. determining an inclination angle relative to a repository plane by the position sensor,
d. comparing the inclination angle to a defined repository angle range,
e. determining a time interval,
f. triggering the switch-off signal if, during the entire time interval, the motion value remains below the threshold and, at the same time, the inclination angle lies in the repository angle range.

A switch-off signal for an electronic medical apparatus including a control device, a motion sensor, a position sensor and a time measuring device is produced by the method according to the invention. A switch-off signal is only activated once a motion value remains continuously below a threshold during the entire time interval and, at the same time, an inclination angle relative to a repository plane lies in the repository angle range. The switch-off signal is activated after the expiry of the time interval if the apparatus is deposited in a defined repository position within the time interval and not moved at the same time.

In this way, a switch-off signal is reliably produced if the medical apparatus is deposited for a period of time that is greater than the defined time interval. The switch-off signal brings about a shutdown of the medical apparatus. Advantageously, a shutdown reduces the energy consumption. The apparatus produces no heat and a possibly present light source is switched off. The period of application and service life of the medical apparatus are increased.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
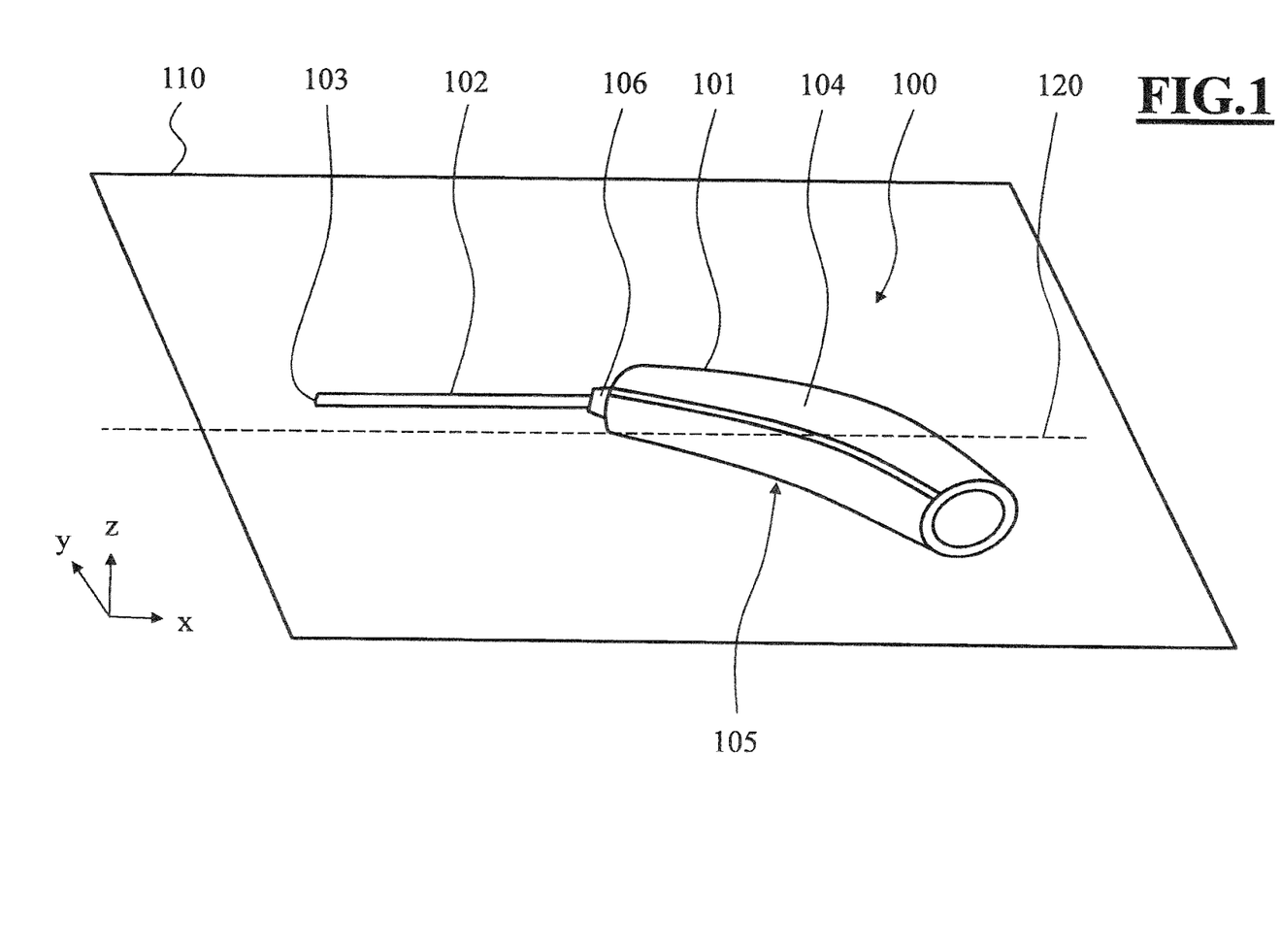
FIG. 1 shows an endoscope which lies in a repository in a laterally horizontal position.

FIG. 1 shows an endoscope which lies in a repository in a laterally horizontal position. An endoscope is an example of a medical apparatus.

An endoscope 100 includes a handpiece 101 and a probe 102. Gripping surfaces 104 are applied to the outer side of the handpiece 101. A control device, an image recording device, an illumination arrangement, a position and motion sensor, a time measuring device and an interface for data transmission are arranged in the interior of the handpiece 101. The endoscope may be coupled, either with a wire or wirelessly, to a monitor or a surgical microscope via a transmission-reception unit. The endoscope may further include an energy store for grid-independent power supply, for example a battery or a rechargeable accumulator or a capacitor with a very high capacitance. By way of example, the control device is a microcontroller.

The probe 102 is arranged on the head portion of the handpiece 101. The probe 102 is a long thin tube which can be introduced into a tissue region. The probe 102 includes a first light guide for illuminating a tissue region and a second light guide which is guided to the image recording device. Optics that are not illustrated here can be arranged at the distal end 103 of the probe 102. A transition element to the handpiece 101 is arranged at the proximal end 106 of the probe 102.

The endoscope 100 is hermetically encapsulated. However, when used during an operation, the endoscope 100 may also be protected by a sterile protective film, which is referred to as a drape.

With a side surface 105, the endoscope 100 lies on a repository plane, a sterile table 110. The sterile table 110 is a repository surface, on which medical tools and apparatuses are provided during an operation. The repository plane forms a horizontal XY-plane. During an operation, the sterile table 110 may be covered by a sterile drape that is not depicted here. With its entire side surface 105, the endoscope 100 lies flat on the sterile table 110. Here, the probe 102 is situated at a parallel distance from the sterile table 110 over its entire length. The plane position of the endoscope 100 on the sterile table 110 is indicated by an auxiliary line 120. The auxiliary line 120 defines a straight line on the surface of the sterile table 110 in the XY-plane. The probe 102 is arranged parallel to the auxiliary line 120.

Figure 2:
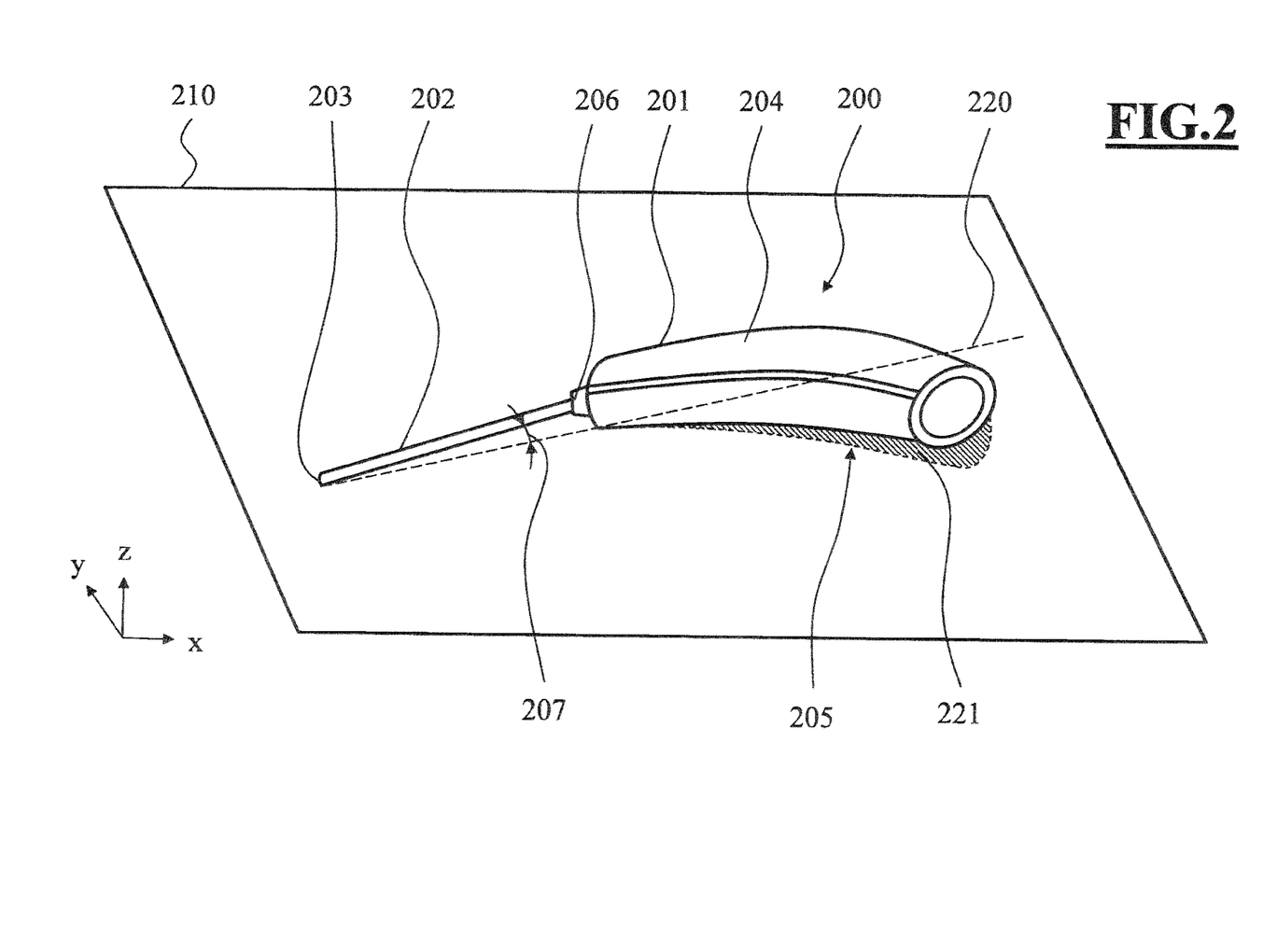
FIG. 2 shows the endoscope as per FIG. 1, which lies laterally in a repository in a tilted position.

FIG. 2 shows the endoscope 100 as per FIG. 1, which lies laterally in a repository in a tilted position. The reference signs have been increased by 100. The endoscope 100 depicted in FIG. 1 lies in a plane on the sterile table 110 with the side surface 105. An endoscope 200 depicted in FIG. 2 differs from the endoscope 100 depicted in FIG. 1 in that the endoscope 200 lies in a laterally tilted manner on a sterile table 210.

Here, a distal end 203 of a probe 202 touches the sterile table 210. An auxiliary line 220 defines a straight line on the surface of the sterile table 210 in an XY-plane. A first point of the auxiliary line is formed by the point of contact of the distal end 203 of the probe 202 with the sterile table 210. A second point of the auxiliary line is defined by the perpendicular projection of a proximal end 206 of the probe 202 on the sterile table 210. Here, an inclination angle 207 is formed between the auxiliary line 220 and the probe 202 in a plane that is perpendicular to the XY-plane. The inclination angle 207 is small and may have an absolute value of up to 10°, for example an absolute value of between 5° and 10°.

In the situations depicted in FIG. 1 and FIG. 2, the endoscope 100, 200 is deposited and is not moved. That is why the motion sensor in each case determines a motion value that is below a threshold. In FIG. 1, the position sensor determines an inclination angle of 0° relative to a repository plane that is formed by the sterile table 110. In FIG. 2, the position sensor detects an inclination angle 207 of 5° relative to the repository plane, the sterile table 210. A switch-off signal is produced since the motion value continuously remains below a threshold in both cases during the entire time interval and, at the same time, the position sensor detects an inclination angle relative to the repository plane that lies in a defined repository angle range of 0° to 10°. This switch-off signal brings about the complete shutdown of the endoscope 100, 200.

In FIG. 1 and FIG. 2, the sterile table 110, 210 forms the repository plane. The sterile table is arranged horizontally. The repository plane may also be formed by a repository arrangement or a holding device, in which the repository plane is defined by a vertical plane or a plane that is arranged obliquely in space. The repository plane can be set by the user of the medical apparatus or of the endoscope 100, 200 as per FIG. 1 and FIG. 2. To this end, the control device may be coupled to a user interface, for example a GUI. Advantageously, a repository plane or repository arrangement may also be detected in combination via an additional Hall sensor or metal sensor that is not depicted here. If, during an operation, the endoscope 100, 200 should be used at an inclination angle that lies in the defined repository angle range, the function for producing the switch-off signal may also be deactivated, for example via the GUI.

Figure 3:
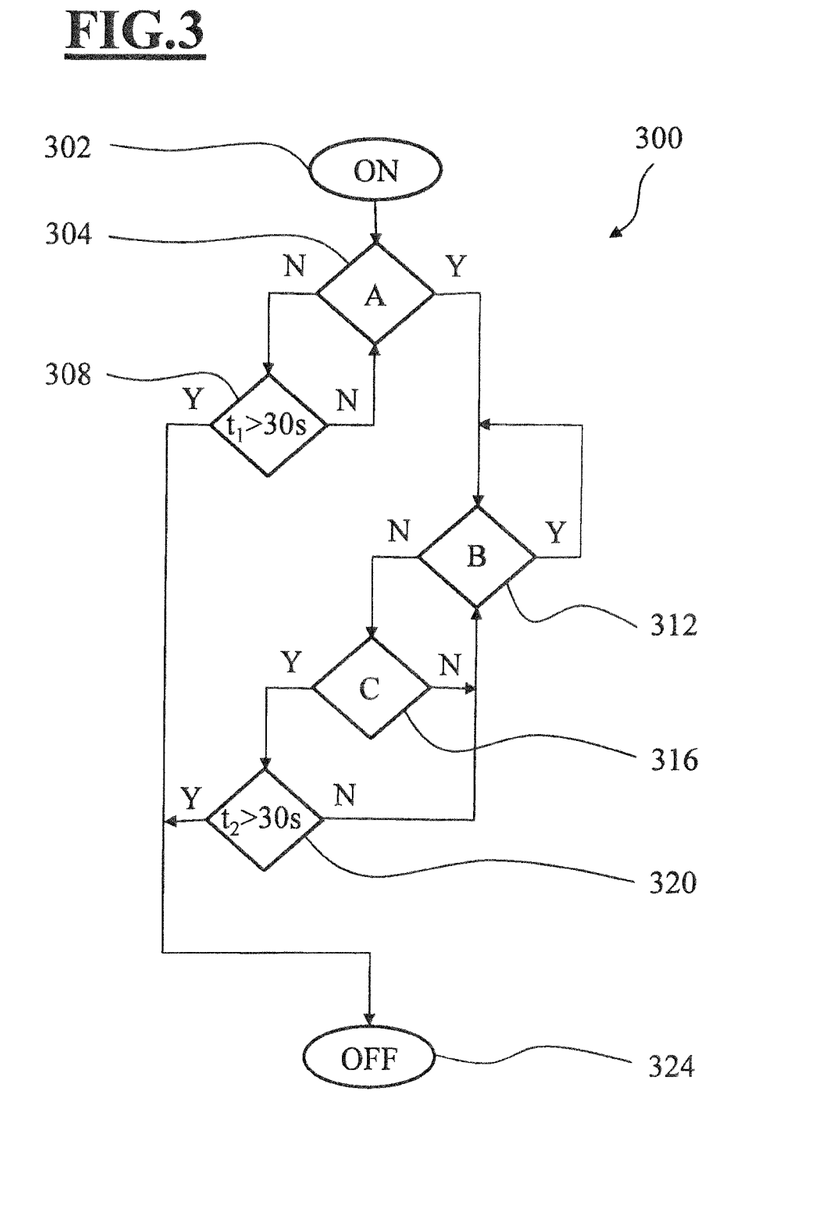
FIG. 3 shows a program flowchart for controlling the switch-off function of the endoscope; and, FIG. 4 shows a block diagram of a medical apparatus.

FIG. 3 depicts a program flowchart 300 for controlling the switch-off signal of the endoscope.

The endoscope is switched on 302 in a first step, for example by actuating a switch-on button. In a subsequent first decision step A, which is denoted by reference sign 304, a check is carried out as to whether the endoscope can be registered to an apparatus group. The apparatus group includes a visualization unit and may also include a surgical microscope, a navigation system or further apparatuses. This check is repeated if the endoscope is not registered to an apparatus group. This check is repeated until a first time interval $t_1$ has expired. The expiry of the first time interval $t_1$ is checked in a second decision step 308. The first time interval $t_1$ is 30 seconds. The endoscope is shut down 324 in a final step after expiry of the first time interval $t_1$. This function is a protection function. It intends to ensure that a receiver which can receive the data from the endoscope is present. If no receiver is found, unnecessary power consumption should be avoided.

If the endoscope finds a receiver in an apparatus group in the first decision step A 304, a check is carried out in a third decision step B, which is denoted by the reference 312, as to whether the "permanently on" function has been activated. If this "permanently on" function has been activated, the endoscope remains switched on until the endoscope is switched off by the user. The "permanently on" function is activated if the endoscope is used in an angular position in which an inclination angle lies in the defined repository angle range. Triggering a switch-off signal can be prevented by the "permanently on" function.

If the "permanently on" function is, or has been, switched off, the program reaches the fourth decision step C, denoted by the reference 316. In the fourth decision step C 316, the parameters of the position and motion data are evaluated. If the endoscope is moved or an inclination angle relative to a repository plane that does not lie in a defined repository angle range is detected, the program jumps back to the third decision step B 312. The endoscope remains activated.

The parameters of the position and motion data are checked in the fourth decision step C 316. If the motion value is below a threshold and, at the same time, the position sensor detects an inclination angle relative to a repository plane that lies in a defined repository angle range, that is, the endoscope was deposited in a pre-set repository position, a check is then carried out in a fifth decision step 320 as to whether a second time interval $t_2$ has already expired. The second time interval $t_2$ is 30 seconds. If the check of the parameters of the position and motion data yields a change within the second time interval $t_2$, for example if the endoscope is moved, that is, the motion value exceeds a threshold, or if the endoscope is picked up by a user again, that is, the detected inclination angle relative to a repository plane no longer lies in the defined repository angle range, the program jumps back to the third decision step again. The endoscope remains activated.

If the second time interval $t_2$ in the fifth decision step has expired without the check of the parameters of the position and motion data in the fourth decision step C 316 yielding a change, that is, the endoscope was deposited in a pre-set repository position, then a switch-off signal is triggered and the endoscope is switched off 324 in a final step.

During the shutdown 324, the endoscope is not put into a standby mode or sleep mode but switched off completely. It is also conceivable that the user is informed that an apparatus shutdown will occur by way of a warning message prior to the shutdown. The endoscope can only be activated by being switched on 302 again, for example by actuating the switch-on button.

In this example, the first time interval $t_1$ and the second time interval $t_2$ are 30 seconds each. The first time interval $t_1$ and the second time interval $t_2$ may also have different values and may respectively be defined to be longer or shorter. The first time interval $t_1$ and the second time interval $t_2$ may also be, for example, 40 seconds, 50 seconds, 60 seconds or any value therebetween.

The pre-set repository position relative to the repository plane may be defined by a lateral position. The lateral repository position includes an angle range, the absolute value of which lies, for example, between 0° and 10°. This angle range is larger if the endoscope is able to tilt in a repository position or the repository surface is not plane or is arranged obliquely in space. The angle range is smaller if the pre-set repository position is obtained by virtue of the endoscope being deposited in a receiving arrangement which promotes a pre-set repository position of the endoscope by way of a specific form. Advantageously, the pre-set repository position may be set by software.

The complete shutdown of the endoscope should occur so that a possible standby current does not lead to a further reduction in the use duration of the endoscope. However, if the standby current is so small that it reduces the service life of the power supply only insubstantially or if it hardly affects the overall energy balance, it is also conceivable that there is a switchover into a standby mode instead of a complete shutdown. A reactivation of the endoscope by way of for example, the position sensor would also be conceivable in this standby mode should this position sensor determine a different position than the repository position.

Figure 4:
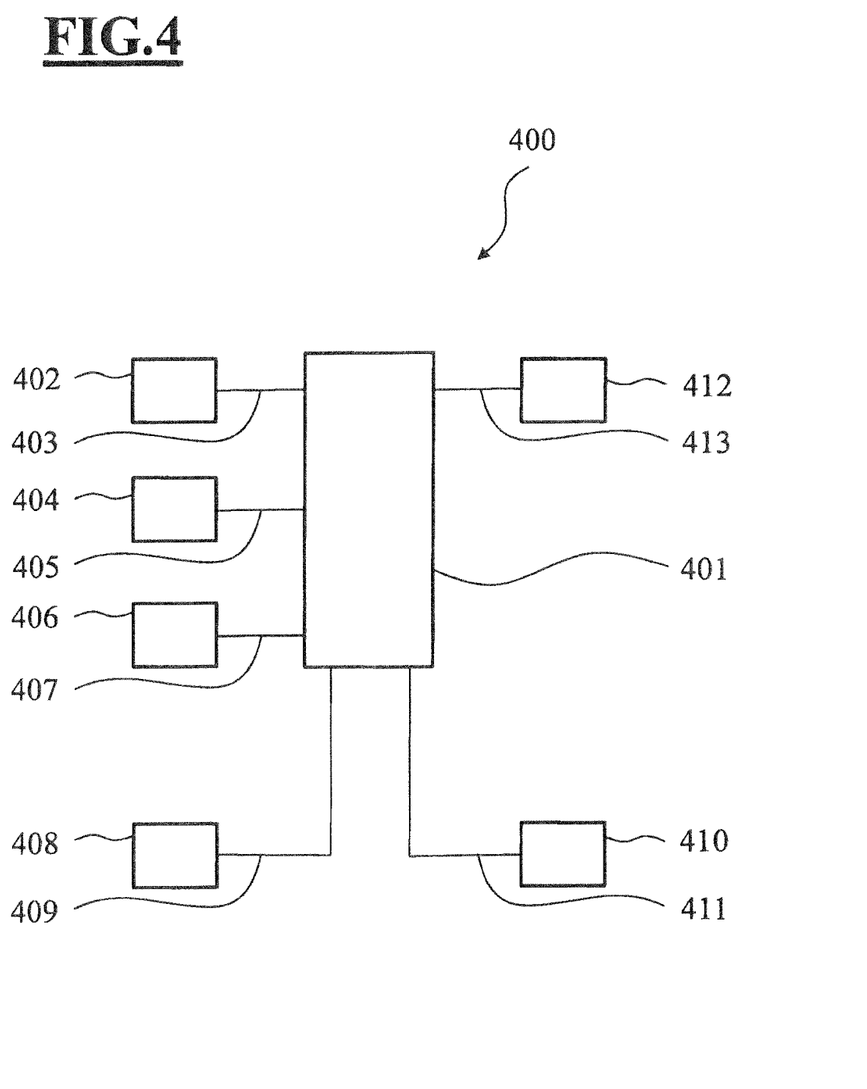

FIG. 4 shows a block diagram of a medical apparatus 400.

The medical apparatus includes a control device 401, a motion sensor 402, a position sensor 404, a time measuring device 406, an illumination arrangement 408, an image recording device 410 and an interface 412. The motion sensor 402 is linked to the control device 401 via a first line 403. The position sensor 404 is linked to the control device 401 via a second line 405. The time measuring device 406 is connected to the control device 401 via a third line 407. The time measuring device 406 may also be formed by a software timer in the control device 401.

The control device 401 can control the illumination arrangement 408 via a fourth line 409. The image recording device 410 is connected to the control device 401 via a fifth line 411. The interface 412 is linked to the control device 401 via a sixth line 413.

By way of example, the control device 401 is a microcontroller. A switch that is not depicted can be connected to the control device 401 for the purposes of switching on the medical apparatus.

The motion sensor 402 and the position sensor 404 may also be formed by a single three-axis gyro sensor. By way of example, the image recording device 410 is a camera. The medical apparatus is coupled to a visualization unit, for example a monitor, display or a data projection of a surgical microscope, via an interface 412. A hand operation switch, a foot switch or a GUI can also be coupled to the control device 401 via the interface 412. It is conceivable that the medical apparatus 400 is also controllable by way of a surgical microscope. The interface 412 may also have a bidirectional transmission and reception unit. In this example, the medical apparatus is supplied with power by way of a battery that is not depicted. The medical apparatus 400 may be an endoscope.

It is understood that the foregoing description is that of the preferred embodiments of the invention and that various changes and modifications may be made thereto without departing from the spirit and scope of the invention as defined in the appended claims.

LIST OF REFERENCE SIGNS 100, 200 Endoscope
101, 201 Handpiece
102, 202 Probe
103, 203 Distal end of the probe
104, 204 Gripping surfaces
105, 205 Side surface
106, 206 proximal end of the probe
110, 210 Sterile table
207 Inclination angle
120, 220 Auxiliary line
300 Program flowchart
302 Switch on
304 First decision step A
308 Second decision step
312 Third decision step B
316 Fourth decision step C
320 Fifth decision step
324 Shutdown
400 Medical apparatus
401 Control device
402 Motion sensor
403 First line
404 Position sensor
405 Second line
406 Time measuring device
407 Third line
408 Illumination arrangement
409 Fourth line
410 Image recording device
411 Fifth line
412 Interface
413 Sixth line

What is claimed is:

1. A medical apparatus comprising:
a control device;
a motion sensor configured to determine a motion value representing a change of location in space of the medical apparatus;
a position sensor configured to detect an angular position in space;
a time measuring device configured to determine a time interval; and,
said control device being configured to generate a switch-off signal if, during the entirety of said time interval, said motion value remains below a threshold and, at the same time, said position sensor detects an inclination angle relative to a repository plane that lies in a defined repository angle range, wherein said repository plane is a plane perpendicular to a vertical direction and said defined repository angle range has an absolute value between 5° and 10°.

2. The medical apparatus of claim 1, wherein the medical apparatus is an endoscope.

3. The medical apparatus of claim 1, wherein said time interval is between 30 seconds and 60 seconds.

4. The medical apparatus of claim 1, wherein said motion sensor and said position sensor are formed by a single three-axis gyro sensor.

5. The medical apparatus of claim 1 further comprising:
an image capturing system configured to capture images; and,
said motion sensor being configured to determine said motion value by analyzing said images captured by the image capturing system.

6. The medical apparatus of claim 1 comprising a metal sensor.

7. The medical apparatus of claim 1 comprising a Hall sensor.

8. The medical apparatus of claim 1 further comprising a cordless power supply having a battery or an accumulator.

9. The medical apparatus of claim 1, wherein a complete shutdown of the medical apparatus is effectable after triggering the switch-off signal.

10. A method for triggering a switch-off signal for a medical apparatus, the medical device including a control device, a motion sensor, a position sensor and a time measuring device, the method comprising the steps:
a. determining a motion value representing a change of location in space of the medical apparatus via the motion sensor;
b. comparing the motion value to a threshold;
c. determining an inclination angle relative to a repository plane via the position sensor, wherein said repository plane is a plane perpendicular to a vertical direction;
d. comparing the inclination angle to a defined repository angle range, wherein the defined repository angle range has an absolute value between 5° and 10°;
e. determining a time interval; and, f. triggering the switch-off signal if, during the entire time interval, the motion value remains below the threshold and, at the same time, the inclination angle lies in the repository angle range.

11. An endoscope comprising:
a probe having a distal end configured to contact a sterile table;
a control device;
a motion sensor configured to determine a motion value representing a change of location in space of the endoscope;
a position sensor configured to detect an angular position in space;
a time measuring device configured to determine a time interval;
said control device being configured to generate a switch-off signal if, during the entirety of said time interval, said motion value remains below a threshold and, at the same time, said position sensor detects an inclination angle relative to a repository plane that lies in a defined repository angle range;
wherein said repository plane and said probe conjointly define said inclination angle in a vertical direction;
said repository plane being a plane perpendicular to the vertical direction; and,
said defined repository angle range having an absolute value between 5° and 10°.

* * * * *